(12) United States Patent
Lan

(10) Patent No.: US 7,547,655 B2
(45) Date of Patent: Jun. 16, 2009

(54) V-P-SI COMPOSITE OXIDE CATALYST PRECURSOR USED FOR PRODUCING MALEIC ANHYDRIDE FROM BUTANCE

(75) Inventor: Renshui Lan, Tianjin (CN)

(73) Assignee: New Tianjin T. & D. Co., Ltd., Tianjin (CN)

( * ) Notice: Subject to any disclaimer, the term of this patent is extended or adjusted under 35 U.S.C. 154(b) by 281 days.

(21) Appl. No.: 10/543,807

(22) PCT Filed: Jan. 30, 2004

(86) PCT No.: PCT/CN2004/000085

§ 371 (c)(1),
(2), (4) Date: Apr. 25, 2006

(87) PCT Pub. No.: WO2004/067170

PCT Pub. Date: Aug. 12, 2004

(65) Prior Publication Data

US 2006/0241310 A1    Oct. 26, 2006

(30) Foreign Application Priority Data

Jan. 30, 2003 (CN) .................. 03 1 01937

(51) Int. Cl.
*B01J 21/02* (2006.01)
*B01J 27/182* (2006.01)
*B01J 23/00* (2006.01)
*B01J 27/198* (2006.01)

(52) U.S. Cl. ............. 502/209; 502/206; 502/214; 502/353

(58) Field of Classification Search .......... 502/206, 502/214, 353, 209
See application file for complete search history.

(56) References Cited

U.S. PATENT DOCUMENTS

| 4,062,873 A | 12/1977 | Harrison |
| 4,064,070 A * | 12/1977 | Harrison ............... 502/209 |
| 4,293,498 A * | 10/1981 | Lemanski et al. ......... 549/259 |
| 4,294,722 A | 10/1981 | Bremer et al. |
| 4,333,853 A * | 6/1982 | Milberger et al. ........ 502/209 |
| 4,371,702 A * | 2/1983 | Bither, Jr. ............. 549/260 |
| 4,562,269 A * | 12/1985 | Moorehead ............ 549/259 |
| 4,713,464 A * | 12/1987 | Fumagalli et al. ....... 549/259 |
| 4,849,539 A | 7/1989 | Bergna |
| 5,108,974 A * | 4/1992 | Davis ................. 502/209 |
| 7,157,403 B2 * | 1/2007 | Weiguny et al. ........ 502/209 |

FOREIGN PATENT DOCUMENTS

| CN | 1059297 | 3/1992 |
| CN | 1133755 | 10/1996 |
| CN | 1282631 | 2/2001 |
| CN | 1303741 | 7/2001 |
| JP | 7-10353 | 2/1995 |
| JP | 9-52049 | 2/1997 |
| WO | WO 03/078059 | * 9/2003 |

OTHER PUBLICATIONS

English Abstract of JP 9-52049 dated Feb. 15, 1997.
Partial English Translation of JP 7-10353 dated Feb. 8, 1995.
Partial English Translation of CN 1059297 dated Mar. 11, 1992.
Partial English Translation of CN 1133755 dated Oct. 23, 1996.
Partial English Translation of CN 1282631 dated Feb. 7, 2001.
Partial English Translation of CN 1303741 dated Jul. 18, 2001.

* cited by examiner

*Primary Examiner*—Patricia L Hailey
(74) *Attorney, Agent, or Firm*—Ladas & Parry LLP

(57) ABSTRACT

The present invention provides a catalyst precursor for producing maleic anhydride by oxidizing butane. Said catalyst precursor is prepared by a process comprising partially reducing $V^{+5}$ to $V^{+4}$ in a mixture of alcohols consisting of isobutanol and benzyl alcohol in a volume ratio of 2.5-5.0, then adding a phosphoric oxy-acid and an alkylsilicon in turn. The catalyst precursor prepared according to said process has a small pore volume, a relatively high bulk density in an appropriate pore size distribution.

17 Claims, No Drawings

V-P-SI COMPOSITE OXIDE CATALYST PRECURSOR USED FOR PRODUCING MALEIC ANHYDRIDE FROM BUTANCE

TECHNICAL FIELD

The present invention relates to a catalyst for production of maleic anhydride. Specifically, the present invention relates to a solid catalyst precursor for production of maleic anhydride by catalytically oxidizing butane, in particular to a V—P—Si composite oxide solid catalyst precursor for production of maleic anhydride in a fixed bed or a fluidized bed.

BACKGROUND ART

Maleic anhydride is an important organic raw material for production of thermosetting resin, unsaturated polyester resin, agricultural chemicals and fine chemicals. Previously, benzene is used as raw material for producing maleic anhydride. However, due to the toxicity, the lack of safety and the environmental harmfulness of benzene, butene is used to replace benzene as raw material for production of maleic anhydride, and apparatus for production of maleic anhydride by catalytically oxidizing butene was established in 1960's. Since butene is expensive, inexpensive and readily obtainable butane is gradually used to replace benzene and butene as raw material for producing maleic anhydride.

By comparing different processes for production of maleic anhydride, the process of using n-butane as raw material for production of maleic anhydride is more profitable than that of using benzene or butene, and said process can be carried out by using fixed bed and/or fluidized bed.

At present, many documents report the studies of catalyst for producing maleic anhydride by using butane as raw material in fixed bed or fluidized bed, wherein various problems in fluidized bed are studied deeply and widely. However, the studies of catalyst useful in fluidized bed are focused on the composition and preparation of V—P—oxide precursor, and many processes for preparation of catalyst precursors are proposed.

CN1059297A discloses a process for preparation of V—P—O type catalyst for production of maleic anhydride by using n-butane as raw material in fluidized bed, said process comprising using industrial grade vanadium pentaoxide and 85% phosphoric acid as raw materials and isobutanol as reducing agent, conducting the reduction reaction under heating condition, then filtering, modifying, adding metal cocatalyst, preparing slurry, and spray drying to obtain microspheroidal catalyst. Said process is relatively long, needs metal cocatalyst and modification, and the obtained catalyst has lower catalytic activity and selectivity.

CN 1133755A discloses a process for preparation of a catalyst for production of maleic anhydride by catalytically oxidizing n-butane in a fluidized bed, said process comprising the preparation of a catalyst precursor and the post-treatment and processing steps. The preparation of the catalyst precursor comprises using vanadium pentaoxide and phosphoric acid as raw materials, hydrazine hydrate as reducing agent, a mixture of benzyl alcohol and isobutanol as solvent, adding iron ions or zirconium ions during the reaction. The obtained precursor together with a silica sol and a gelling agent form a supported catalyst slurry. The slurry is then dried and dewatered, activated under certain atmosphere and temperature, and finally molded and screened to obtain the catalyst product. Said process is relatively long and complex as well.

CN1282631A discloses a process for preparation of a V—P—O catalyst, said process comprising heating and refluxing vanadium pentaoxide and concentrated hydrochloric acid, then adding phosphoric acid and continuously refluxing, cooling, and adding zirconium nitrate, ammonium molybdate and zinc acetate. This catalyst has a complex composition, but has a lower catalytic activity and selectivity.

CN1303741A describes a process for the preparation of a composite V—P—O catalyst for production of maleic anhydride by catalytically oxidizing n-butane, said process comprising adding a ceria-based composite oxide as oxygen-storing body to a VPO catalyst in order to increase the available oxygen quantity of the catalyst system. The catalyst prepared by said process has a complex composition and contains expensive rare earth oxides.

U.S. Pat. No. 5,108,974 discloses a process for preparation of a V—P-oxide catalyst precursor, said process comprising heating and reducing vanadium pentaoxide ($V_2O_5$) to vanadium tetraoxide ($V_2O_4$) in an alcohol solvent in the presence of a mixture of alkyl silicate and phosphoric acid, and precipitating the product with additional phosphoric acid in the presence of alkyl silicate.

U.S. Pat. No. 4,294,722 discloses a process for preparation of an oxidization catalyst containing the mixed oxides of vanadium and phosphorus which is particularly effective for the oxidization of n-butane, said process comprising dissolving vanadium pentaoxide in isobutanol, heating and refluxing for about 16 hours, dissolving phosphoric acid in isobutanol and adding the solution to the filtrate, and refluxing the resultant mixture for 8 hours, cooling and collecting precipitate to obtain a catalyst precursor. The catalyst obtained by said process has a lower selectivity and yield of maleic anhydride.

U.S. Pat. No. 4,062,873 discloses a process for preparation of a V—P—Si-oxide, said process comprising coprecipitating a vanadium oxide and an alkyl orthosilicate in an organic medium to form a coprecipitate of vanadium oxide and silica precursor, coprecipitating phosphorus either simultaneously with the vanadium oxide and alkyl orthosilicate coprecipitation or thereafter to thereby obtain the catalyst precursor; and calcining said catalyst precursor to obtain a silica-containing catalyst.

According to the above statements, the catalysts prepared according to the processes in the prior art still have disadvantages such as lower yield and selectivity of maleic anhydride, longer preparation process, etc. For overcoming these disadvantages, the present inventor carries out a long-term deep study and develop a catalyst precursor that is prepared by reducing a pentavalent vanadium compound in an organic medium, reacting the reduction product with phosphoric acid under heating condition, and then reacting the resultant product with an alkylsilicon under heating condition, wherein said catalyst precursor has an appropriate pore size distribution, a small pore volume, and a relatively high bulk density. Thus, the catalyst prepared from said catalyst precursor has more catalytically active components per unit volume than the catalyst in the prior art, has a high conversion rate of maleic anhydride, is capable of further improving the yield of maleic anhydride based on n-butane.

Contents of the Invention

Hence, the object of the present invention is to provide a V—P—Si composite oxide catalyst precursor for production of maleic anhydride by catalytically oxidizing butane, in particular to a V—P—Si composite oxide catalyst precursor for a fixed bed or a fluidized bed.

Another object of the present invention is to provide a process for the preparation of a V—P—Si composite oxide catalyst precursor for production of maleic anhydride by catalytically oxidizing butane, in particular a catalyst precursor for a fixed bed or a fluidized bed.

The third object of the present invention is to provide an improved process for production of maleic anhydride by catalytically oxidizing butane.

The V—P—Si composite oxide catalyst precursor for production of maleic anhydride by catalytically oxidizing butane, in particular the catalyst precursor for a fixed bed or a fluidized bed is composed of a composite oxide of vanadium, phosphorus and silicon, and has a molar ratio of V:P:Si=0.77-1.1:1:0.1-1. The pore size distribution as measured by ASAP2405 adsorption detector indicates that more than 90% pores have a pore size of greater than 100 Å, less than 10% pores have a pore size of smaller then 100 Å, and the average pore size is 130-180 Å. The pore volume is 0.01-0.10 ml/g, preferably 0.02-0.06 ml/g. The bulk density is 0.80-1.00 g/cm$^3$, preferably 0.85-0.90 g/cm$^3$.

According to the above statements, the catalyst precursor of the present invention has an appropriate pore size distribution, so that the obtained catalyst has a smaller pore volume and a higher bulk density than the catalyst in the prior art, and thus has more effective active sites for catalytic oxidation per unit of catalyst. Hence, when the catalyst of the present invention is used in a fixed bed and a fluidized bed, the molar yield of maleic anhydride based on butane is more than 5 mol % and 10 mol % higher than the catalyst in the prior art, respectively.

The process for preparing the catalyst precursor of the present invention comprises:
(1) Adding vanadium pentaoxide to a mixture of alcohols (having a volume ratio of isobutanol/benzyl alcohol=2.5-5.0), heating and refluxing for 0.5-2 hours;
(2) Adding a phosphorus oxy-acid to the product formed in step (1) at a rate of 1.0-10 g/min under reflux heating condition, and continuously heating and refluxing for 0.5-5 hours;
(3) Adding an alkylsilicon to the product formed in step (2) at a rate of 0.5-5 g/min under reflux heating condition, and continuously heating and refluxing for 6-12 hours;
(4) Cooling, filtering, washing the filter cake with an organic solvent, and drying to obtain the catalyst precursor.

The process for preparing the catalyst precursor of the present invention is characterized in that the raw materials are added stepwise, and the reduction reaction is carried out stepwise. Namely, the vanadium compound is firstly added to a mixture of alcohols and heated to refluxing in order to at least partially reduce V$^{+5}$ to V$^{+4}$, then the phosphorus oxy-acid is added under refluxing condition, and the alkylsilicon is added dropwise after the phosphorus oxy-acid is added completed.

Another characteristic of the present invention is that the phosphorus oxy-acid and the alkylsilicon are added dropwise in different rates, so that the reaction is carried out slowly and the crystal grows in a certain rate to obtain a catalyst precursor having appropriate pore size, pore volume and bulk density.

The organic solvent used in the present invention is isobutanol and/or benzyl alcohol. If a mixture of benzyl alcohol and isobutanol is used, the volume ratio of isobutanol:benzyl alcohol is 2.5-5.0.

The pentavalent vanadium compound used in the present invention is not specially restricted, but preferably is vanadium pentaoxide. For accelerating the reaction, vanadium pentaoxide is preferably ground to have a particle size of less than 100 µm, preferably less than 30 µm.

The phosphorus oxy-acid used in the present invention is not specially restricted as well, but preferably is phosphoric acid, more preferably 85 wt % phosphoric acid.

The organosilicon compound used in the present invention is not specially restricted as well, but preferably is tetramethoxysilicane and tetraethoxysilicane.

In the present invention, the reduction reaction of vanadium pentaoxide in an organic medium, i.e., alcohols, is performed under heating and refluxing condition, generally for 0.5-2 hours, preferably 1-2 hours, and under a stirring condition having a stirring rate of 100-1000 rpm, preferably 300-800 rpm.

In the present invention, the rate of adding phosphorus oxy-acid, preferably phosphoric acid is not specially restricted, and generally is 1.0-10 g/min, preferably 1-9 g/min, more preferably 3-8 g/min.

In the present invention, the rate of adding alkylsilicon is not specially restricted, and generally is 0.5-5.0 g/min, preferably 1.0-5.0 g/min, more preferably 1.0-4.5 g/min.

In the present invention, phosphorus oxy-acid and alkylsilicon are added separately, and their addition rates are identical or different, preferably the rate of adding phosphorus oxy-acid is greater than the rate of adding alkylsilicon, if only the (VO)$_2$H$_4$P$_2$O$_9$ crystal grows at a desired rate.

After the catalyst precursor is obtained according to the process of the present invention, it can be molded with a conventional binder according to the general knowledge and common molding methods in the art to form any desired shape, such as sheet, column, pill, ring, ball, granule, etc.

The present invention is described by the following examples in detail, but the present invention is not restricted by these examples. The protection scope of the present invention is proposed in the annexed claims.

EXAMPLE 1

980 ml isobutanol and 200 ml benzyl alcohol were added in a 2 L glass reactor equipped with a heater, a mechanical stirrer and a condenser under stirring, then 60 g vanadium pentaoxide was added, and the reaction system was heated and refluxed for 1 hour. After this, 95 g 85% phosphoric acid was added dropwise at a rate of 2.3 g/min, and then 50 g tetramethoxysilicane was added dropwise at a rate of 3 g/min. After further refluxing for 12 hours, the reaction system was cooled to room temperature, filtered under vacuum to obtain a filter cake. The filter cake was washed with 500 ml isobutanol, and dried at 150° C. for 2 hours to obtain about 110 g product. The preparation conditions and the evaluation results of properties are listed in Table 1.

EXAMPLE 2

Except for not adding benzyl alcohol, the Example 2 was carried out identically according to the Example 1. About 110 g product was obtained. The preparation conditions and the evaluation results of properties are listed in Table 1.

EXAMPLE 3

Except for not adding alkylsilicon, the Example 3 was carried out identically according to the Example 1. About 110 g product was obtained. The preparation conditions and the evaluation results of properties are listed in Table 1.

EXAMPLE 4

Except for reducing vanadium pentaoxide with a mixture solution of alcohols and a part of phosphoric acid (about 30 g) and alkylsilicon (20 g) and then adding dropwise the residual phosphoric acid and alkylsilicon, the Example 4 was carried out identically according to the Example 1. About 110 g product was obtained. The preparation conditions and the evaluation results of properties are listed in Table 1.

EXAMPLE 5

Except for reducing vanadium pentaoxide with a mixture solution of alcohols and all alkylsilicon and then adding dropwise phosphoric acid, the Example 5 was carried out identically according to the Example 1. About 110 g product was obtained. The preparation conditions and the evaluation results of properties are listed in Table 1.

EXAMPLE 6

Except for pouring alkylsilicon into the reactor, i.e., not controlling the charging rate of alkylsilicon, the Example 6 was carried out identically according to the Example 1. About 110 g product was obtained. The preparation conditions and the evaluation results of properties are listed in Table 1.

EXAMPLE 7

Except for pouring phosphoric acid into the reactor, i.e., not controlling the charging rate of phosphoric acid, the Example 7 was carried out identically according to the Example 1. About 110 g product was obtained. The preparation conditions and the evaluation results of properties are listed in Table 1.

EXAMPLE 8

Except for reducing vanadium pentaoxide with a mixture solution of alcohols and all phosphoric acid and then adding dropwise alkylsilicon, the Example 8 was carried out identically according to the Example 1. About 110 g product was obtained. The preparation conditions and the evaluation results of properties are listed in Table 1.

especially as a catalyst for production of maleic anhydride by catalytically oxidizing butane in a fixed bed or a fluidized bed. The catalytic activity evaluation of said catalyst indicates that said catalyst has a high activity and selectivity, and has a maleic anhydride yield of 10 mol % high than the conventional catalyst in the art.

According to the above statements, the present invention provides a V—P—Si composite oxide catalyst precursor for the production of maleic anhydride by catalytically oxidizing butane, a process for the preparation the same, and a use of said catalyst precursor in the production of maleic anhydride by catalytically oxidizing butane. It is very clear that the person skilled in the art may further modify or improve the present invention, and these modifications the present invention if they do not depart from the spirits of the present invention. The scope of the present invention is proposed by the annexed claims.

What is claimed is:

1. A VPSi composite oxide catalyst precursor for preparing a catalyst for the production of maleic anhydride, characterized in that said catalyst precursor has a pore size distribution of: more than 90% pores having a pore size of greater than 100 Å, less than 10% pores having a pore size of smaller than 100 Å, and having a pore volume of 0.01-0.10 ml/g.

2. The catalyst precursor according to claim 1, characterized in that the bulk density is 0.80-1.00 g/cm3.

3. The catalyst precursor according to claim 1, characterized in that the molar ratio of V:P:Si is 0.77-1.1:1:0.1-1.

4. A process for preparing a catalyst precursor according to claim 1, characterized in that said process comprises the following steps:
   a) adding a pentavalent vanadium compound to a mixture of alcohols, heating and refluxing for 0.5-2 hours;
   b) adding a phosphorus oxy acid to the product formed in step (1) at a rate of 1.0-10 g/min under reflux heating condition;

TABLE 1

| Example No. | Total weight of raw materials | Adding stepwise phosphoric acid and alkylsilicon | Controlling the charging rate | Catalyst precursor | | | Evaluation of catalyst in a fixed bed Yield % |
|---|---|---|---|---|---|---|---|
| | | | | Average pore size Å | Pore volume ml/g | Bulk density g/ml | |
| 1 | Yes | Yes | Yes | 148 | 0.03 | 0.94 | 62 |
| 2 | No | Yes | Yes | 147 | 0.045 | 0.80 | 45 |
| 3 | No | Yes | Yes | 129 | 0.04 | 0.82 | 50 |
| 4 | Yes | No | Yes | 154 | 0.07 | 0.79 | 57 |
| 5 | Yes | No | Yes | 179 | 0.09 | 0.52 | 48 |
| 6 | Yes | Yes | No | 160 | 0.075 | 0.75 | 54 |
| 7 | Yes | Yes | No | 172 | 0.08 | 0.6 | 50 |
| 8 | Yes | No | Yes | 185 | 0.10 | 0.48 | 45 |

The results of Table 1 indicate that when the total raw materials are identical, a V—P—Si composite oxide catalyst precursor having an appropriate pore size distribution, a small pore volume and a high bulk density is obtained by adding stepwise raw materials to a mixture of alcohols, heating and refluxing to reduce at least partial $V^{+5}$ to $V^{+4}$, then adding phosphoric acid and alkylsilicon in turn under refluxing condition, and controlling reaction rate thereof to carry out the reaction slowly. After said V—P—Si composite oxide catalyst precursor is molded according to molding techniques well known in the art, it can be used as a catalyst for production of maleic anhydride by catalytically oxidizing butane, c) adding an alkylsilicon to the product formed in step (2) at a rate of 0.5-5 g/min under reflux heating condition, and continuously heating and refluxing for 6-12 hours;
   d) cooling, filtering, washing the filter cake with an organic solvent, and drying to obtain the catalyst precursor.

5. The process according to claim 4, characterized in that the steps (2) and (3) are carried out in twice.

6. The process according to claim 4, characterized in that the phosphorus oxy acid is added dropwise after the reduction reaction between the pentavalent vanadium compound and the mixture of alcohols is completed.

7. The process according to claim 4, characterized in that the mixture of alcohols is a mixture of isobutanol and benzyl alcohol in a volume ratio of 2.5-5.0.

8. The process according to claim 4, characterized in that the rate of adding the phosphorus oxy acid is 1-9 g/min.

9. The process according to claim 8, characterized in that the rate of adding the phosphorus oxy acid is 3-8 g/min.

10. The process according to claim 4, characterized in that the phosphorus oxy acid is phosphoric acid.

11. The process according to claim 10, characterized in that the phosphoric acid is 85 wt % phosphoric acid.

12. The process according to claim 4, characterized in that the rate of adding alkylsilicon is 1.0-5.0 g/min.

13. The process according to claim 12, characterized in that the rate of adding alkylsilicon is 1.0-4.5 g/min.

14. The process according to claim 4, characterized in that the alkylsilicon is tetramethoxysilicane or tetraethoxysilicane.

15. A method for producing maleic anhydride comprising the steps of mixing butane and the catalyst precursor of claim 1 to catalytically oxidize the butane and obtain maleic anhydride.

16. The catalyst precursor according to claim 1, characterized in that the pore volume is from 0.02-0.06 ml/g.

17. The catalyst precursor according to claim 16, characterized in that the bulk density is 0.80-1.00 g/cm3.

* * * * *